United States Patent
Yasushi et al.

(10) Patent No.: US 7,922,655 B2
(45) Date of Patent: Apr. 12, 2011

(54) ENDOSCOPE ATTACHMENT AND ENDOSCOPE

(75) Inventors: Yagi Yasushi, Hyogo (JP); Echigo Tomio, Osaka (JP); Sagawa Ryusuke, Osaka (JP)

(73) Assignee: Osaka University, Osaka (JP)

( * ) Notice: Subject to any disclaimer, the term of this patent is extended or adjusted under 35 U.S.C. 154(b) by 1139 days.

(21) Appl. No.: 11/630,956

(22) PCT Filed: Jul. 4, 2005

(86) PCT No.: PCT/JP2005/012321
§ 371 (c)(1),
(2), (4) Date: Dec. 28, 2006

(87) PCT Pub. No.: WO2006/004083
PCT Pub. Date: Jan. 12, 2006

(65) Prior Publication Data
US 2008/0045797 A1 Feb. 21, 2008

(30) Foreign Application Priority Data
Jul. 2, 2004 (JP) .................. 2004-197355

(51) Int. Cl.
*A61B 1/06* (2006.01)
*A61B 1/04* (2006.01)

(52) U.S. Cl. ........ 600/173; 600/109; 600/127; 600/129; 600/160; 600/170

(58) Field of Classification Search .......... 600/127, 600/129, 160, 172, 175, 109, 170, 171, 173, 600/176, 177; 396/322, 332; 359/627, 633
See application file for complete search history.

(56) References Cited

U.S. PATENT DOCUMENTS

| | | | | |
|---|---|---|---|---|
| 2,987,960 A | * | 6/1961 | Sheldon | 359/367 |
| 3,413,067 A | * | 11/1968 | Froio | 600/160 |
| 3,548,808 A | * | 12/1970 | Nagashige et al. | 600/173 |
| 3,918,438 A | * | 11/1975 | Hayamizu et al. | 600/168 |
| 4,403,273 A | | 9/1983 | Nishioka | |
| 4,699,463 A | * | 10/1987 | D'Amelio et al. | 385/118 |

(Continued)

FOREIGN PATENT DOCUMENTS

JP 54-177787 12/1979

(Continued)

OTHER PUBLICATIONS

Kuriyama et al., Image Pickup Device and Endoscopic System Provided With the Same, Aug. 20, 2002, English translation of JP 2002-233494.*

(Continued)

*Primary Examiner* — John P Leubecker
*Assistant Examiner* — Jeffrey H Chang
(74) *Attorney, Agent, or Firm* — Wenderoth, Lind & Ponack, L.L.P.

(57) ABSTRACT

An endoscope attachment enables an endoscope to capture images of areas in front and at the sides of the endoscope. The endoscope attachment has a transparent attaching part which is used to attach the endoscope attachment to a probe of the endoscope and has two through-holes. A cylindrical transparent image capturing part is used to enable a camera of the probe to capture images and has a trumpet-shaped second mirror on the outer wall of the image capturing part and a wide angle lens with a hyperboloid in the image capturing part. A first mirror is formed at a part of the hyperboloid of the wide angle lens.

8 Claims, 14 Drawing Sheets

U.S. PATENT DOCUMENTS

| | | | |
|---|---|---|---|
| 4,838,247 A * | 6/1989 | Forkner | 600/173 |
| 4,846,154 A * | 7/1989 | MacAnally et al. | 600/171 |
| 5,518,501 A * | 5/1996 | Oneda et al. | 600/127 |
| 5,756,988 A * | 5/1998 | Furuta | 250/208.1 |
| 5,940,126 A * | 8/1999 | Kimura | 348/294 |
| 6,095,970 A | 8/2000 | Hidaka et al. | |
| 6,130,783 A * | 10/2000 | Yagi et al. | 359/627 |
| 6,142,932 A | 11/2000 | Morizumi | |
| 6,387,044 B1 | 5/2002 | Tachibana et al. | |
| 6,450,950 B2 * | 9/2002 | Irion | 600/170 |
| 6,736,773 B2 * | 5/2004 | Wendlandt et al. | 600/173 |
| 7,408,703 B2 * | 8/2008 | Matsuki et al. | 359/365 |
| 2005/0038317 A1 * | 2/2005 | Ratnakar | 600/101 |
| 2009/0112061 A1 * | 4/2009 | Kim et al. | 600/109 |

FOREIGN PATENT DOCUMENTS

| | | |
|---|---|---|
| JP | 57-125731 | 8/1982 |
| JP | 59-41322 | 3/1984 |
| JP | 62-86323 | 4/1987 |
| JP | 4-279141 | 10/1992 |
| JP | 6-160734 | 6/1994 |
| JP | 07-113962 | 5/1995 |
| JP | 9-101465 | 4/1997 |
| JP | 10-229965 | 9/1998 |
| JP | 10-311954 | 11/1998 |
| JP | 11-125773 | 5/1999 |
| JP | 11-318808 | 11/1999 |
| JP | 2001-299679 | 10/2001 |
| JP | 2002-233494 | 8/2002 |
| JP | 2002-341409 | 11/2002 |
| JP | 2003-164418 | 6/2003 |
| WO | 2004/008185 | 1/2004 |

OTHER PUBLICATIONS

Supplementary European Search Report issued Jan. 28, 2009 in corresponding European patent application No. 05765238.0.

* cited by examiner

PRIOR ART

ENDOSCOPE ATTACHMENT AND ENDOSCOPE

BACKGROUND OF THE INVENTION

1. Technical Field

The present invention relates to an endoscope attachment, and more particularly to an endoscope attachment attached to an endoscope used to image the inside of digestive organs, and the endoscope.

2. Background Art

Conventionally, in the field of medical practice, gastrointestinal endoscopes have been used for inspecting digestive organs. The gastrointestinal endoscopes are classified to an upper endoscope used to inspect esophagus, stomach and duodenum, and a lower endoscope used to inspect rectum and large intestine. A probe of the upper endoscope is inserted from an oral cavity, while a probe of the lower endoscope is inserted from an anus. In addition to the inspection of the digestive organs for discovering suspected lesions, the above endoscopes need to cut and collect the discovered lesions to be examined. Therefore, at an end portion of the endoscope (distal end of the endoscope), not only a camera but also a lighting for illuminating the interior of the organs, forceps for cutting and collecting lesions, and a water injection nozzle for removing secretion of the organs from the camera are equipped. A physician inserts a probe of the endoscope into the digestive organs, and performs diagnosis, collection of lesion, and treatment, viewing images monitored by the camera equipped at the end portion.

FIG. 14A is an external view of the probe of the conventional endoscope, and FIG. 14B is a top view of an end portion of the probe (distal end of the probe) of the same endoscope (see Patent Reference 1).

The distal end of the probe of the endoscope has a camera 1000, two lightings 1010 and 1020, a forceps opening 1030, and a water injection nozzle 1040.

[Patent Reference 1] Japanese Patent Application Laid-Open No. 11-318808

However, although the above-structured conventional endoscope has a view field in front of distal end of the probe in a direction of inserting the endoscope, which is convenient to insert probe and maneuver the forceps, there is a problem that the inner surfaces of the digestive organs which are to be actually observed are positioned along the sides of the probe, which makes it difficult for the physician to inspect the surfaces. Moreover, since digestive organs has folds, a side of the fold which is a rear side from the inserting the distal end of the probe becomes often a blind area. Therefore, it is difficult to display an image of the rear side of the fold, which causes a problem of a high possibility of overlooking lesions. Especially at the rear side of the fold in the area where the organ is significantly bent, observation is almost impossible, which results in a quite high possibility of overlooking lesions. Here, in order to address the above problems, a method is conceived to use a wide angle lens for the camera, but there is a drawback that distortion of the lens becomes great near the side surface of the organ to be observed. Further, there is another method disclosed in Japanese Patent Application Laid-Open Nos. 2002-33943 and 2002-341409, to have view fields in front (front view field) and also at the sides of the endoscope (side view field), by equipping an omnidirectional mirror to the camera lens. However, when the omnidirectional mirror is used to view with a wide angle, it is necessary to illuminate the wide view field, but the lighting of the conventional endoscope can illuminate only a narrow forward view field. Therefore, the method of merely using the omnidirectional mirror for the camera lens of the endoscope fails to capture images of the organ surfaces at the sides of the endoscope, so that the above problems have not been solved.

Therefore, in view of the above problems, the first object of the present invention is to provide an endoscope attachment which enables an endoscope to eliminate any blind areas and prevent a physician from overlooking nidus.

Furthermore, the second object of the present invention is to provide an endoscope attachment which enables an endoscope to capture images of area in front and at the sides of the endoscope.

Means to Solve the Problems

In order to achieve the above objects, the endoscope attachment according to the present invention is attachable to a distal end of a probe of an endoscope used to image a digestive organ. The endoscope attachment includes: a view field obtaining part for obtaining a front view field and a side view field for the probe; and an illumination light providing part for diffusing illumination light illuminating an area in front of the probe in order to provide the illumination light to an area at side of the endoscope attachment. Here, the view field obtaining part may be an optical-lens transparent member which has a predetermined-shaped surface on a part of which a mirror is formed, an image of the area at side of the probe may be captured by the camera of the probe via the mirror, an image of the area in front of the probe may be captured by the camera via a part of the predetermined-shaped surface of the optical-lens transparent member, on the part the mirror not being formed, the optical-lens transparent member may be a wide angle lens, the predetermined-shaped surface may be a convex surface, the predetermined-shaped surface may be a hyperboloid, and the predetermined-shaped surface may be a spherical surface. Further, the view field obtaining part may obtain an omnidirectional view field for the probe.

Furthermore, the view field obtaining part may be a ring-shaped mirror having an opening, an image of the area at side of the probe may be captured by the camera of the probe via the mirror, and an image of the area in front of the probe may be captured by the camera through the opening of the mirror. Here, the endoscope attachment may have a support member by which the mirror is fixed to the endoscope attachment.

Still further, the illumination light providing part may be a first mirror which has a trumpet shape flaring out in order to shield the illumination light illuminating an area in front of the probe (hereinafter, referred to as a trumpet shape), the illumination light providing part may have a plurality of the first mirrors, the illumination light providing part may be a conical or cylindrical transparent optical member which protrudes ahead of the probe, the mirror may also have a convex shape, and the mirror may also have a plane shape. Still further, the illumination light providing part may be the ring-shaped mirror which is used also as the view field obtaining part, and the opening of the mirror may be positioned at a range where forceps can move.

Thereby, a view angle at the side of the endoscope is enlarged to obtain a view field at the backside of the distal end of the probe in order to capture images of digestive organ, not only of the areas merely positioned at the sides of the endoscope, but also of front and rear sides of folds. Therefore, it is possible to realize an endoscope attachment which enables an endoscope to eliminate any blind areas and prevent a physician from overlooking nidus. Further, the endoscope attachment has a simple structure, so that it is possible to realize an endoscope attachment which is easily cleansed thereby preventing spread of the disease to somebody else. Furthermore, the structure of the existing endoscope which has already been used in many medical institutions does not need to be changed but can still be used, so that it is possible to realize an endoscope attachment which enables the endoscope to expand its functions easily and with a low cost. Still further, the mirror enables the camera to capture images of areas at the sides of the probe, and also enables illumination light emitted from the probe to illuminate the areas, which results in unnecessity of separately equipping: a member for having the camera capture the image of the areas at the sides of the probe; and a member for providing the illumination light to the areas, so that it is possible to realize an endoscope attachment which has a simple structure.

Moreover, the endoscope has view fields in front and at the sides of the endoscope, and illumination light can illuminate areas in front and at the sides of the endoscope, so that it is possible to realize an endoscope attachment which enables the endoscope to have not only the imaging system but also a lighting suitable for the imaging system thereby capturing images of the areas in front of and at the sides of the endoscope.

Furthermore, the first mirror may diffuse a part of the illumination light illuminating the area in front of the probe, in order to provide the part of the illumination light to an area at side of the endoscope attachment.

Thereby, illumination light surely illuminate areas in front of the endoscope attachment, so that it is possible to realize an endoscope attachment which enables the prove to be easily operated.

Furthermore, the view field obtaining part may be an optical-lens transparent member having a predetermined-shaped surface on a part of which a second mirror is formed, the transparent member being arranged in a cylindrical housing of the endoscope attachment, the first mirror may be arranged on an outer wall of the housing, and the second mirror may prevent the illumination light illuminating the area in front of the probe from being irradiated on the first mirror.

Thereby, the illumination light emitted from the probe is prevented from being irradiated on the camera as incident light, so that it is possible to realize an endoscope attachment which prevents a part of image captured by the endoscope from being too brightened.

Furthermore, the endoscope attachment may further include a transparent attaching part, which has two through-holes, to be used to attach the endoscope attachment to the probe, wherein relative positions of the holes in the endoscope attachment correspond to relative positions of a forceps opening and a water injection nozzle of the probe, respectively.

Thereby, positions of the forceps opening and the water injection nozzle in the probe are adjusted to two holes in the endoscope attachment, respectively, thereby adjusting a position of the camera, so that it is possible to realize an endoscope attachment which is easily attached to the endoscope.

Furthermore, the opening may be positioned at an area of the mirror, on the area the illumination light being regularly reflected to the camera.

Thereby, the illumination light emitted from the probe is prevented from being irradiated on the camera as incident light, so that it is possible to realize an endoscope attachment which prevents a part of image captured by the endoscope from being too brightened.

SUMMARY OF THE INVENTION

According to the endoscope attachment of the present invention, it is possible to realize an endoscope attachment which enables an endoscope to eliminate any blind areas and prevent a physician from overlooking nidus. Further, it is possible to realize an endoscope attachment which enables an endoscope to capture images of areas in front and at the sides of the endoscope. Furthermore, it is possible to realize an endoscope attachment which enables the endoscope to expand its functions easily and with a low cost. Still further, it is possible to realize an endoscope attachment which is easily cleansed thereby preventing spread of the disease to somebody else. Still further, it is possible to realize an endoscope attachment which is easily attached to the endoscope.

Thus, according to the present invention, it is possible to provide an endoscope attachment which enables an endoscope to eliminate any blind areas and prevent a physician from overlooking nidus. As a result, the present invention makes extremely significant contributions to the field of medical instruments and the progress of medical science.

NUMERICAL REFERENCES

| | |
|---|---|
| 42 | hyperboloidal mirror |
| 100 | attaching part |
| 110, 1200, 1300 | image capturing part |
| 120, 130, 1100 | holes |
| 140 | convex part |
| 150 | wide angle lens |
| 151 | first mirror |
| 171 | second mirror |
| 200, 1000 | camera |
| 210, 1040 | water injection nozzle |
| 220, 1030 | forceps opening |
| 230, 240, 1010, 1020 | lightings |
| 820, 830, 860, 870 | rod lens |
| 840, 850 | ball lens |
| 900, 1330 | transparent members |
| 1110 | hollow |
| 1120, 1130, 1140 | light shielding films |
| 1210, 1310 | mirrors |
| 1211, 1311 | openings |
| 1220, 1320 | support bars |

DETAILED DESCRIPTION OF THE INVENTION

The following describes an endoscope attachment according to the embodiments of the present invention with reference to the drawings.

First Embodiment

Figure 1A:
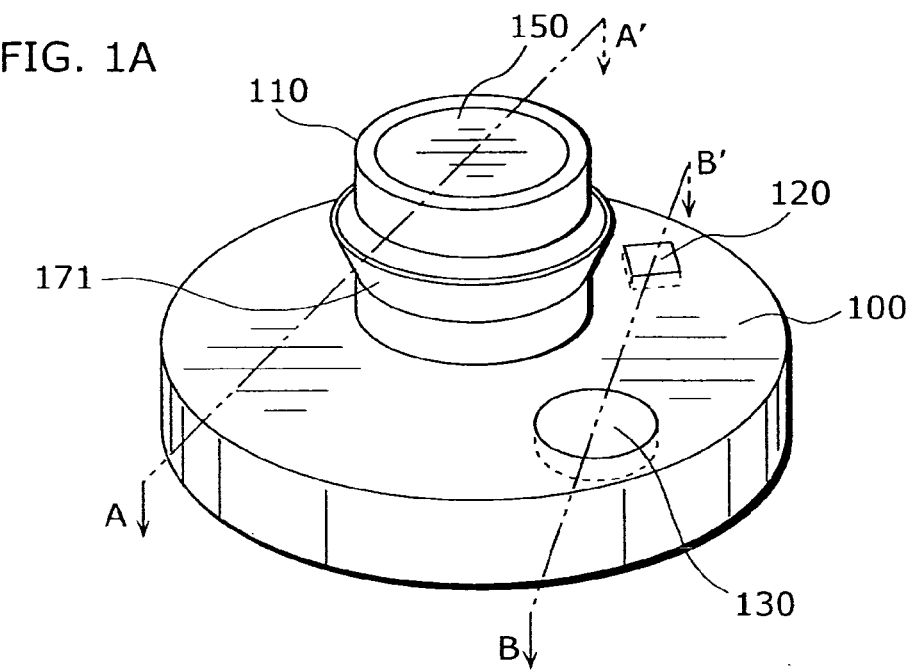
FIG. 1A is an external view of an endoscope attachment according to the first embodiment.
Figure 1B:
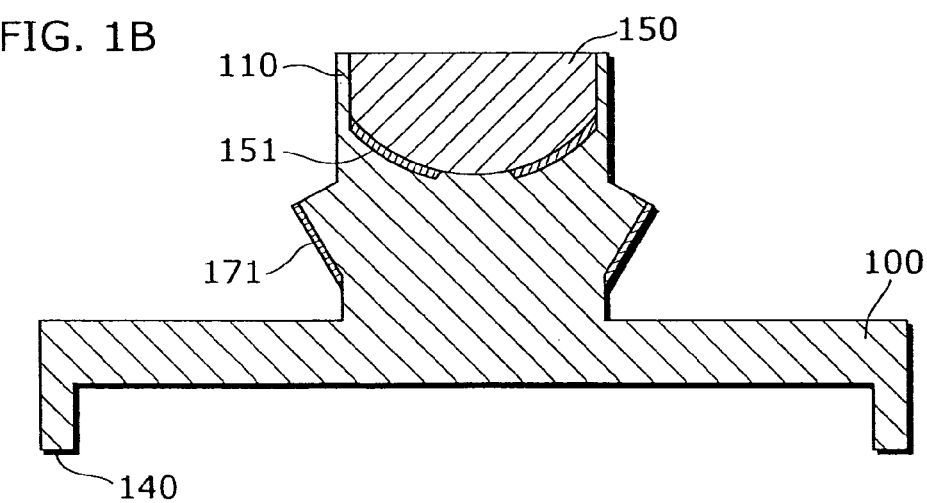
FIG. 1B is a cross sectional view (taken along line A-A' of FIG. 1A) of the endoscope attachment according to the first embodiment.
Figure 1C:
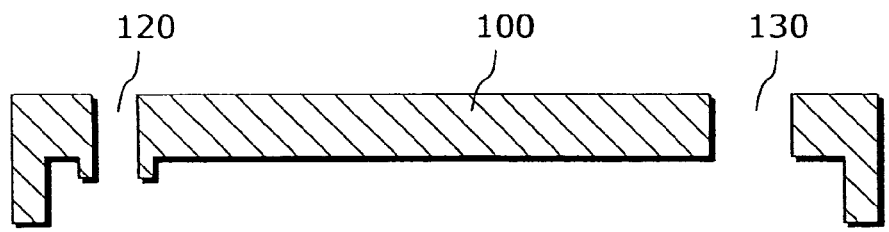
FIG. 1C is a cross sectional view (taken along line B-B' of FIG. 1A) of the endoscope attachment according to the first embodiment.

FIG. 1A is an external view of an endoscope attachment according to the first embodiment. FIGS. 1B and 1C are cross sectional views (taken along lines A-A' and B-B' of FIG. 1A) of the endoscope attachment.

The endoscope attachment according to the first embodiment, which is made of transparent material such as glass or acrylic, is attachable to a probe of an endoscope. The endoscope attachment has: a flat-plate-shaped attaching part 100 which is arranged to cover the distal end of the probe in order to attach the endoscope attachment to the probe; a cylindrical image capturing part 110 which is used to enable a camera in the probe to capture images, and formed on a surface of the attaching part 100 which is the opposite side of the surface contact with the distal end of the probe, in other words, on a top surface of the attaching part 100.

In the attaching part 100, two holes 120 and 130 are formed to pass through the attaching part 100. The hole 120 is a hole for a water injection nozzle in the probe. That is, the hole 120 prevents that any shielding exists in front of the water injection nozzle after the endoscope attachment being attached. The hole 130 is a hole for forceps opening in the probe. That is, the hole 130 prevents that any shielding exists in front of the forceps opening after the endoscope attachment being attached. Here, relative positions of the holes 120 and 130 in the attaching part 100 and the image capturing part 110 correspond to relative positions of the water injection nozzle, the forceps opening, and the camera at the distal end of the probe.

On the bottom surface of the attaching part 100, a convex part 140 is formed along the outer periphery of the attachment part 100. The endoscope attachment is combined to the endoscope, by being engaged with the convex part 140 to the distal end of the probe of the endoscope.

In the cylinder of the image capturing part 110, a wide angle lens 150 having hyperboloid is arranged with the hyperboloid facing down. The wide angle lens 150 is a lens for collecting light incident from a front view field with a wide angle. Thereby, as shown in a cross sectional view of the endoscope attachment of FIG. 2, on an image plane of the camera, a wide-angle view field is imaged in a central narrow view angle, so that it is possible to obtain a wide range view field with minimum resolution required for operating of the prove and the like.

Figure 2:
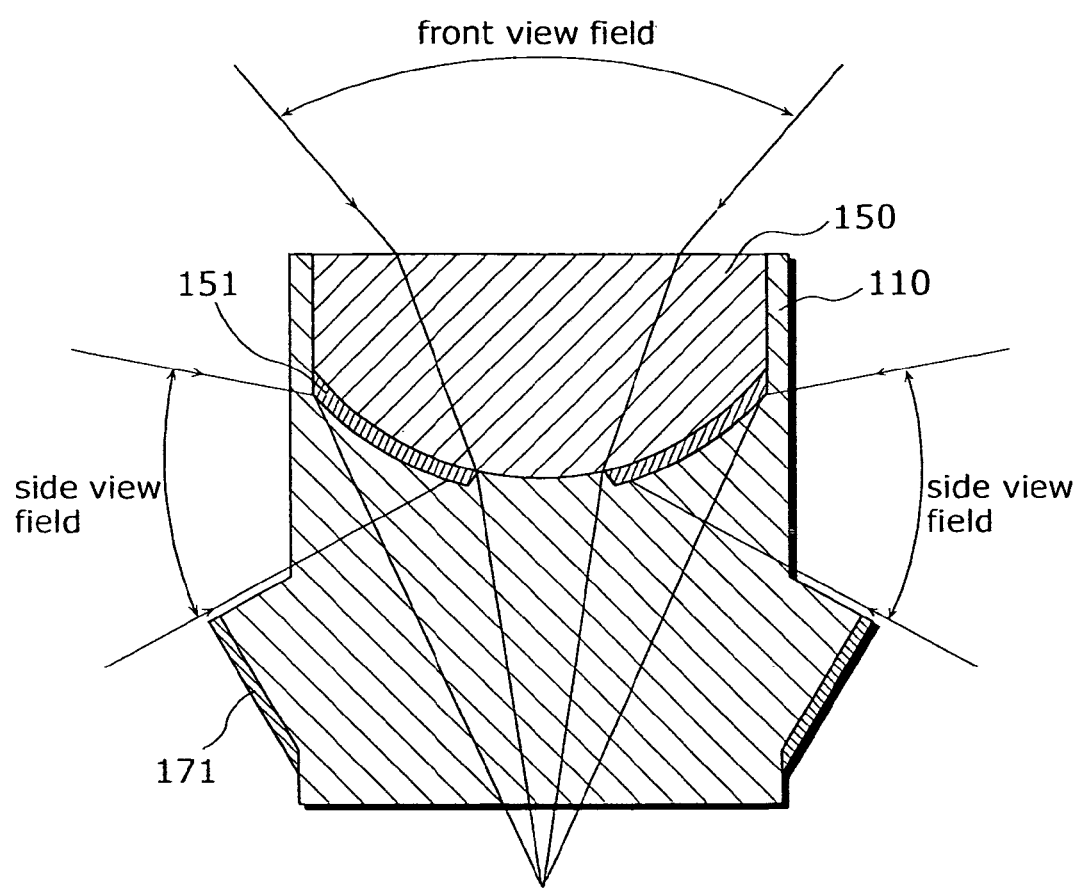
FIG. 2 is a cross sectional view of the endoscope attachment according to the first embodiment.

Here, on the hyperboloid of the wide angle lens 150, the first mirror 151 is formed to reflect light incident from a wide-angle side view field to be irradiated on the camera. Thereby, a hyperboloidal mirror, which forms one sheet of the two-sheeted hyperboloid, is formed, so that, as shown in FIG. 2, a wide-angle side view field is imaged on the image plane of the camera. Here, in order to enable the camera to capture image of an area in front of the endoscope, the first mirror 151 is not formed at center of the hyperboloid of the wide angle lens 150. The above first mirror 151 is formed by masking the center of the hyperboloid and depositing metal such as aluminium, for example. It is assumed that the center of the camera lens in the probe is located at a focal point of the other sheet of the two-sheeted hyperboloid. An example of the camera using the hyperboloidal mirror is HyperOmni Vision proposed by Yamazawa et al., which will be described in detail further below. Note that the side view field obtained by the hyperboloidal mirror is adjacent to the front view field on the image plane but these view fields are not contiguous.

The image capturing part 110 has a part of a flaring shape (hereinafter referred to as a trumpet shape) so that the illumination light illuminating the area in front of the probe is shielded. On an outer wall of the cylinder of the image capturing part 110, the trumpet-shaped second mirror 171 is formed. The second mirror 171 diffuses the illumination light incident from the probe and prevents the illumination light of the probe from being irradiated on the first mirror 151. Here, if all of the illumination light is irradiated on the second mirror 171, the illumination light is not provided to an area in front of the endoscope attachment, which makes it difficult to operate the probe. Therefore, a position and a size of the second mirror 171 are adjusted, so that a part of the illumination light can be provided to the area in front of the endoscope attachment and the illumination light can be prevented from being irradiated on the first mirror 151.

Figure 3A:
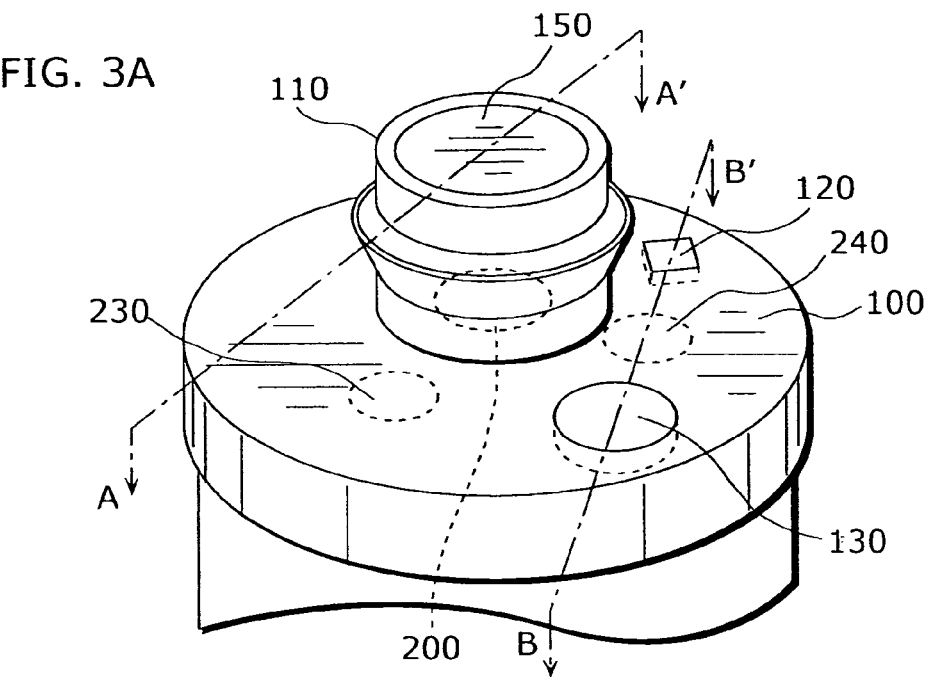
FIG. 3A is an external view of a distal end of a probe of an endoscope to which the endoscope attachment according to the first embodiment is attached.
Figure 3B:
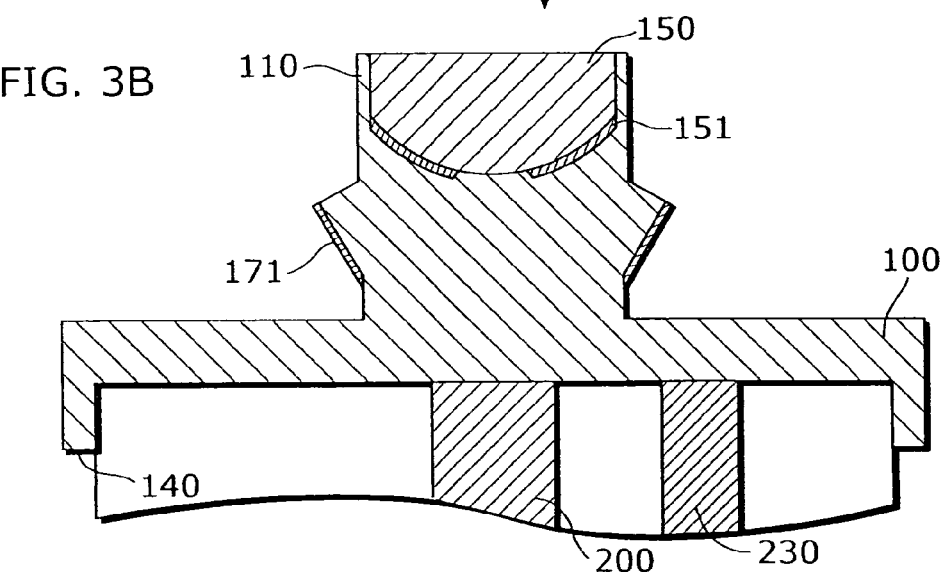
FIG. 3B is a cross sectional view (taken along line A-A' of FIG. 3A) of the distal end of the probe of the endoscope to which the endoscope attachment according to the first embodiment is attached.
Figure 3C:
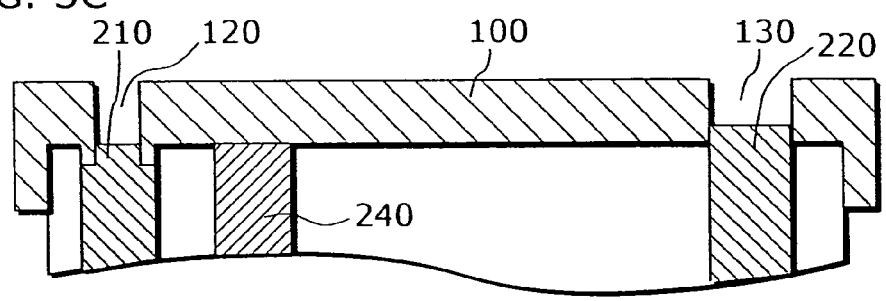
FIG. 3C is a cross sectional view (taken along line B-B' of FIG. 3A) of the distal end of the probe of the endoscope to which the endoscope attachment according to the first embodiment is attached.

FIG. 3A is an external view of the distal end of the probe to which the above-structured endoscope attachment is attached. FIGS. 3B and 3C are cross sectional views (taken along lines A-A' and B-B' of FIG. 3A) of the distal end of the probe.

A camera 200 in the probe is to be positioned immediately under the image capturing part 110 of the endoscope attachment, in order to capture images of areas in front and at sides of the endoscope, through the endoscope attachment. Here, the position of the camera 200 is adjusted to be fit to the image capturing part 110, using the holes 120 and 130 of the endoscope attachment, the water injection nozzle 210, and the forceps opening 220. More specifically, for the positioning, the convex part arranged at an opening of the hole 120 is engaged with an opening of the water injection nozzle 210, and a convex part arranged at an opening of the forceps opening 220 is engaged with an opening of the hole 130. This is possible when the relative positions of the holes 120 and 130 in the attaching part 100 and the image capturing part 110 correspond to the relative positions of the camera 200, the water injection nozzle 210, and the forceps opening 220 at the distal end of the probe.

Two lightings 230 and 240 in the probe are to be positioned immediately under the attaching part 100, in order to provide the illumination light from the outside of the cylinder of the image capturing part 110 to the front side of the probe. A part of this illumination light is diffused by the second mirror 171 in the endoscope attachment and thereby illuminates areas at the sides of the endoscope attachment, while other parts of the illumination light illuminates an area in front of the endoscope attachment.

Next, the imaging processing, in which an input is an image signal obtained in the camera using the hyperboloidal mirror, is described.

Figure 4:
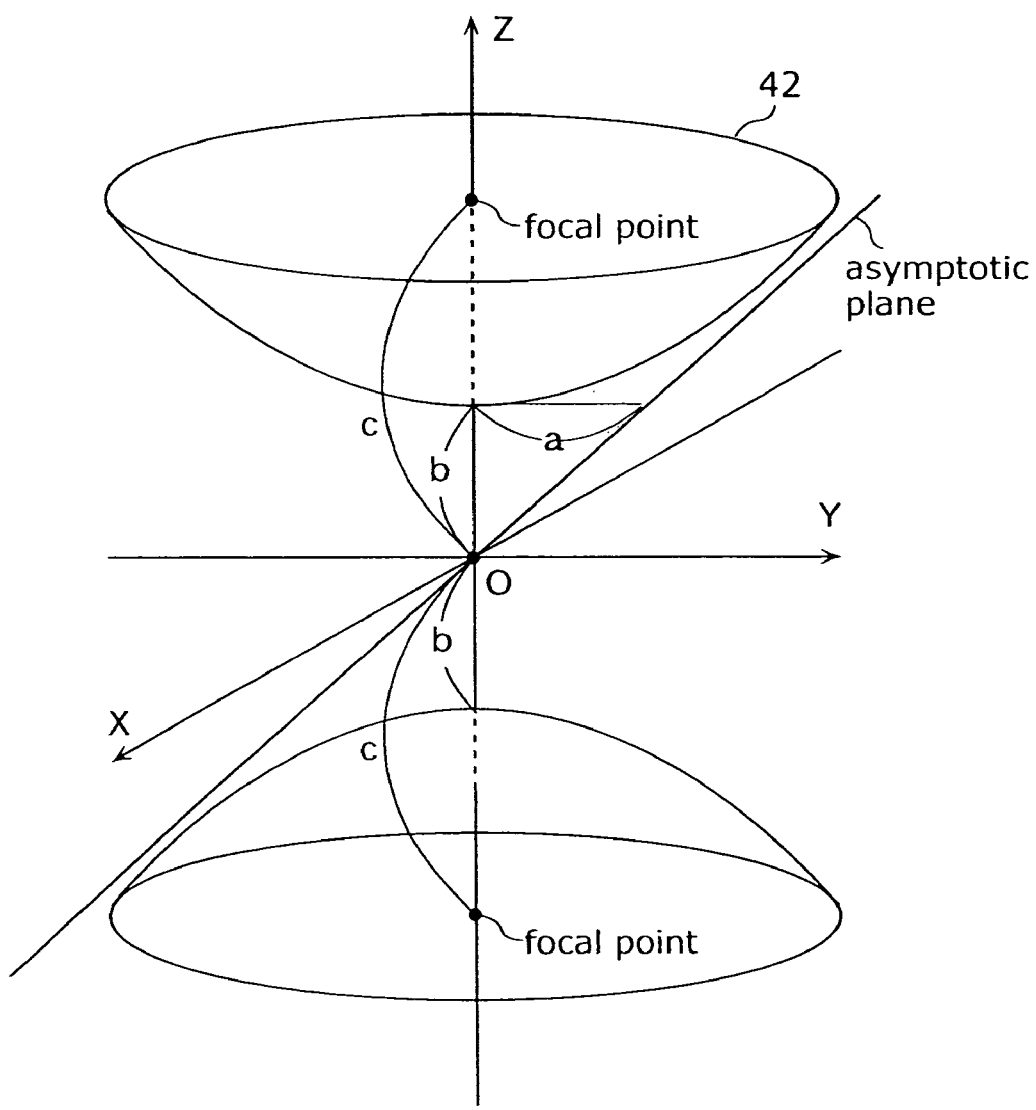
FIG. 4 is a view showing a two-sheeted hyperboloid.

Referring to FIG. 4, the hyperboloidal mirror 42 uses as a mirror the sheet of the two-sheeted hyperboloid that is located in the region where Z>0. The two-sheeted hyperboloid is a curved surface obtained by rotating a hyperbolic curve about the real axis (Z-axis). The two-sheeted hyperboloid has two focal points (0,0,+c) and (0,0,−c). Where

[expression 1]

$$c=\sqrt{a^2+b^2}.$$

Figure 5:
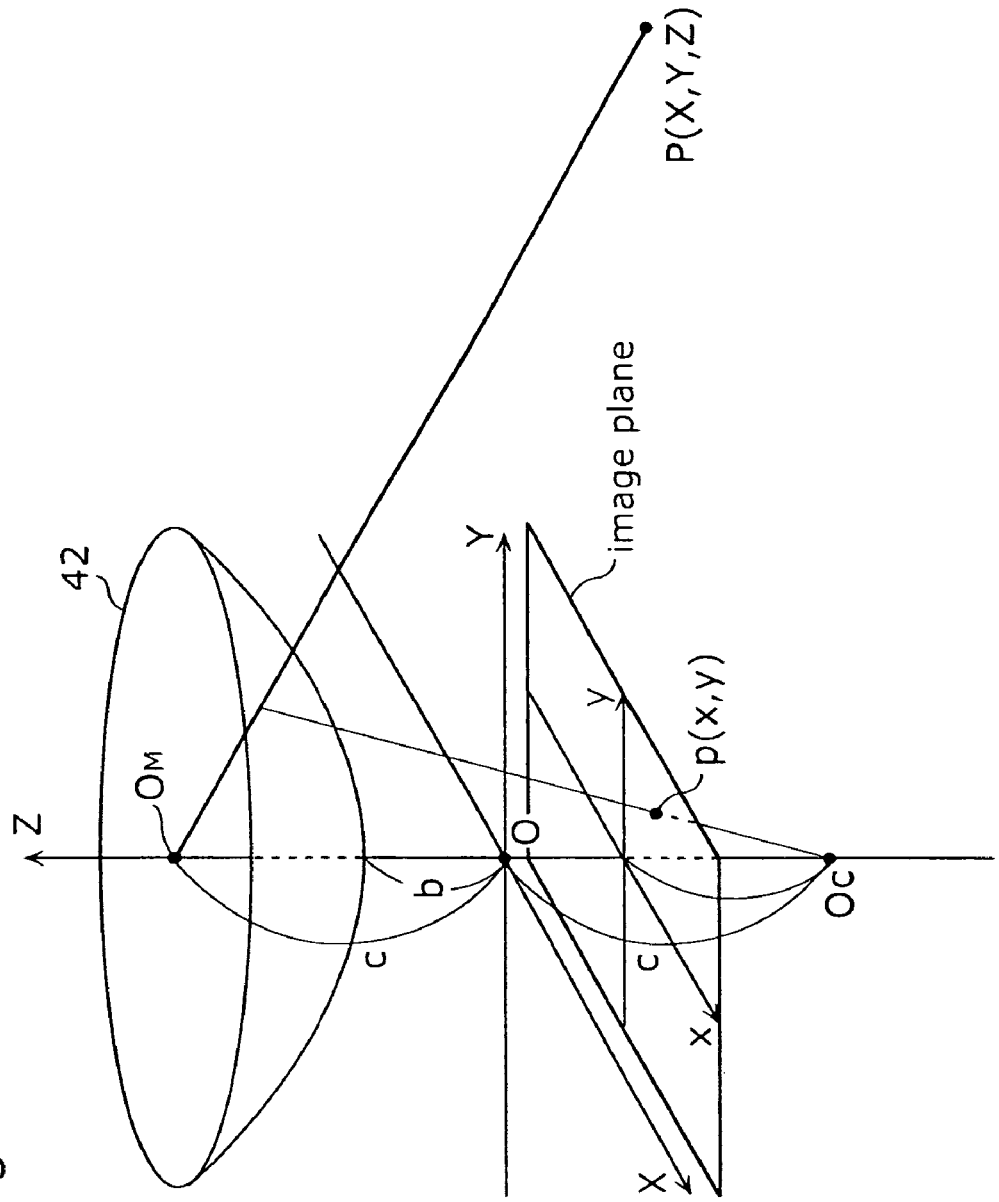
FIG. 5 is a view showing a structure of an omnidirectional camera.

Here, consider a three-dimensional coordinate system O-XYZ having the Z-axis as the vertical axis as shown in FIG. 5. In this case, the two-sheeted hyperboloid is expressed by the following equation (1).

[expression 2]

$$\frac{X^2+Y^2}{a^2}-\frac{Z^2}{b^2}=-1 \quad (1)$$

Note that constants a and b define the shape of a hyperbolic curve. Referring to FIG. 5, the omnidirectional camera HyperOmni Vision is composed of the hyperboloidal mirror 42, which is provided in the region where Z>0 so as to face downward in the vertical direction, and an imaging unit (not shown), which is provided therebelow so as to face upward in the vertical direction. In this case, the hyperboloidal mirror 42 and the imaging unit are positioned such that the focal point OM of the hyperboloidal mirror 42 and the lens center OC of the camera are located at two focal points (0,0,+c) and (0,0,−c), respectively, of the two-sheeted hyperboloid. The image plane xy is assumed to be a plane parallel to the XY plane and distanced by a focal distance f of the camera from the lens center OC of the imaging unit. The reflection surface of the hyperboloidal mirror 42, the focal point OM of the hyperboloidal mirror 42 and the lens center OC of the camera are expressed by the following equation (2).

[expression 3]

$$\begin{cases} \text{Mirror surface} & \frac{X^2+Y^2}{a^2}-\frac{Z^2}{b^2}=-1 (Z>0) \quad (2) \\ \text{Focal point } OM \text{ of the mirror} & (0,0,+c) \\ \text{Lens center } OC \text{ of the camera} & (0,0,-c) \end{cases}$$

Figure 6:
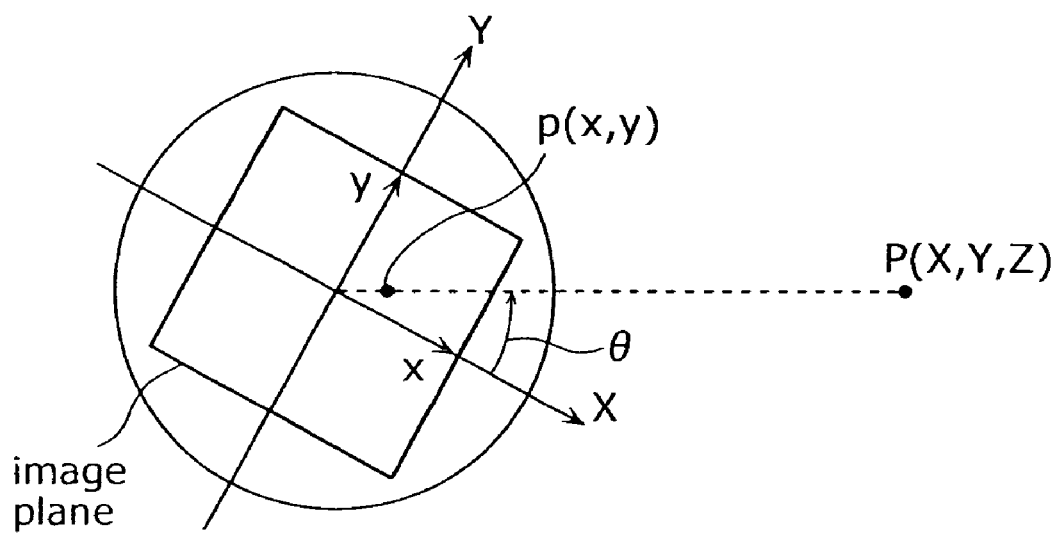
FIG. 6 is the first view showing a relationship between an arbitrary point in space and a mapping point on image.

Referring to FIG. 6, when a mapping point on an image that corresponds to an arbitrary point P(X,Y,Z) in space is taken as p(x,y), the azimuth angle at the point P is expressed by the following equation (3).

$$\tan = Y/X = y/x \quad (3)$$

Specifically, the azimuth angle at the point P defined by Y/X is obtained by calculating the azimuth angle at the mapping point p defined by y/x. In this manner, the azimuth angle of a target object within a 360-degree panoramic region directly appears as the map azimuth of the object on the image plane.

Figure 7:
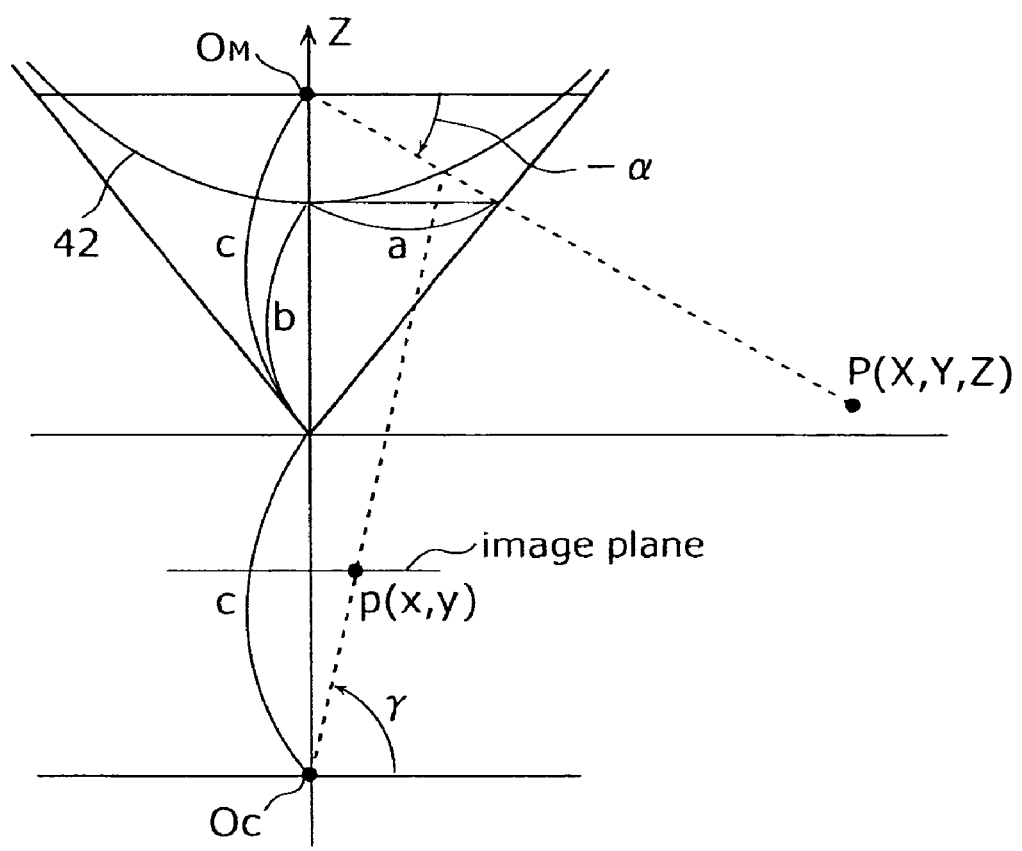
FIG. 7 is the second view showing a relationship between an arbitrary point in space and a mapping point on image.

Referring to FIG. 7, supposing a vertical section including the point P and the Z-axis, the relationship of the following equation (4) is established between the point P and the mapping point p.

[expression 4]

$$\begin{cases} Z=\sqrt{X^2+Y^2}\tan\alpha+c \\ \alpha=\tan^{-1}\frac{(b^2+c^2)\sin\gamma-2bc}{(b^2-c^2)\cos\gamma} \\ \gamma=\tan^{-1}\frac{f}{\sqrt{x^2+y^2}} \end{cases} \quad (4)$$

Specifically, the azimuth angle and the depression angle at the point P from the focal point OM of the hyperboloidal mirror 42 is uniquely obtained based on the mapping point p(x,y) by providing the lens center OC of the camera at the focal position of the hyperboloid. In this case, the focal point OM of the hyperboloidal mirror 42 is fixed, and therefore an input image can be transformed to an image (a panoramic image) viewed from the focal point OM of the hyperboloidal mirror 42, which is obtained by rotating the camera about the vertical axis, or a normal camera image.

The omnidirectional camera HyperOmni Vision is disclosed in detail in "Kazumasa Yamazawa et al., 'Omnidirectional Visual Sensors for Navigation of Mobile Robots', Journal of the Institute of Electronics, Information and Communication Engineers, D-II, Vol. J79-D-II, No. 5, pp. 698-707 (May, 1996)", etc.

As described above, according to the endoscope attachment of the first embodiment, the first mirror 151 forms the hyperboloidal mirror. Thereby, a view angle of the side view field is enlarged to obtain images of an omnidirectional view field, thereby capturing images of not only the areas merely positioned at the sides of the endoscope, but also front and rear sides of folds. Therefore, the endoscope attachment of the first embodiment can be realized as an endoscope attachment which enables an endoscope to eliminate any blind areas and prevent a physician from overlooking nidus.

Further, according to the endoscope attachment of the first embodiment, the endoscope attachment has: the second mirror 171 which provides a part of the illumination light of the probe to the areas at sides of the endoscope attachment; the wide angle lens 150 which enables the camera 200 to capture images of an area in front of the endoscope; and the first mirror 151 which enables the camera 200 to capture images of areas at the sides of the endoscope. Thereby, the endoscope has the front view field and the side view field, and the illumination light can be provided in front and at the sides of the endoscope, so that the endoscope attachment of the first embodiment can be realized as an endoscope attachment which enables the endoscope to have not only the imaging system but also a lighting suitable for the imaging system thereby capturing images of the areas in front of and at the sides of the endoscope.

Furthermore, according to the endoscope attachment of the first embodiment, the endoscope attachment is attached to the distal end of the probe of the endoscope and then used. Thereby, the structure of the existing endoscope which has already been used in many medical institutions does not need to be changed but can still be used, so that the endoscope attachment of the first embodiment can be realized as an endoscope attachment which enables the endoscope to expand its functions easily and with a low cost.

Still further, according to the endoscope attachment of the first embodiment, the endoscope attachment has: the attaching part 100; and the image capturing part 110 in which the wide angle lens 150 is arranged. Thereby, the endoscope attachment has a simple structure, so that the endoscope attachment of the first embodiment can be realized as an endoscope attachment which is easily cleansed thereby preventing spread of the disease to somebody else.

Still further, according to the endoscope attachment of the first embodiment, the second mirror 171 prevents the illumination light of the probe from being irradiated on the first mirror 151. Thereby, the illumination light emitted from the probe is prevented from being irradiated on the camera as incident light, so that the endoscope attachment of the first embodiment can be realized as an endoscope attachment which prevents a part of image captured by the endoscope from being too brightened.

Still further, according to the endoscope attachment of the first embodiment, the endoscope attachment has the holes 120 and 130, and the position of the camera 200 is adjusted to be fit to the image capturing part 110, by engaging the water injection nozzle 210 and the forceps opening 220 of the endoscope with the holes 120 and 130. Thereby, complicated processes are not necessary to attach the endoscope attachment to the endoscope, so that the endoscope attachment of the first embodiment can be realized as an endoscope attachment which is easily attached to the endoscope.

Figure 8A:
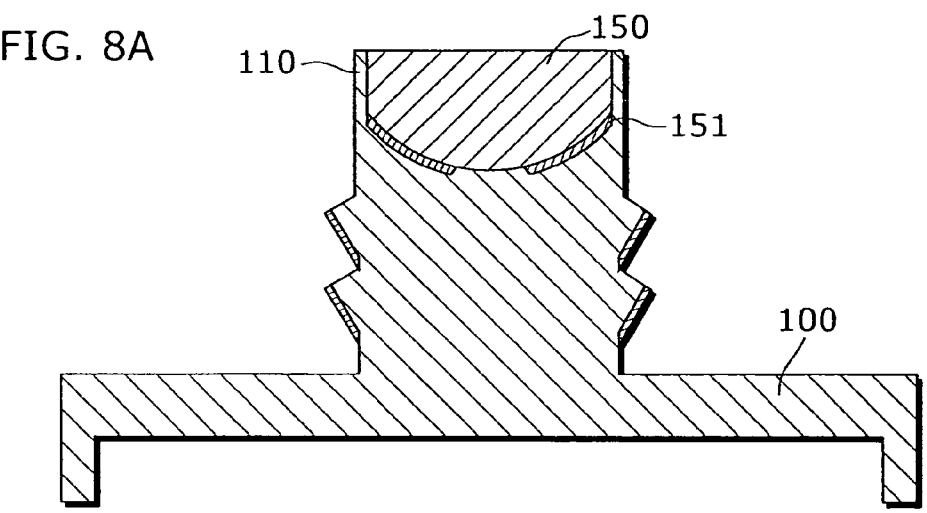
FIG. 8A is a cross sectional view of the first variation of the endoscope attachment according to the first embodiment.

Note that, as shown in FIG. 8A, on the outer wall of the cylinder of the image capturing part 110, there may be two or more, for example two, trumpet-shaped parts.

Figure 8B:
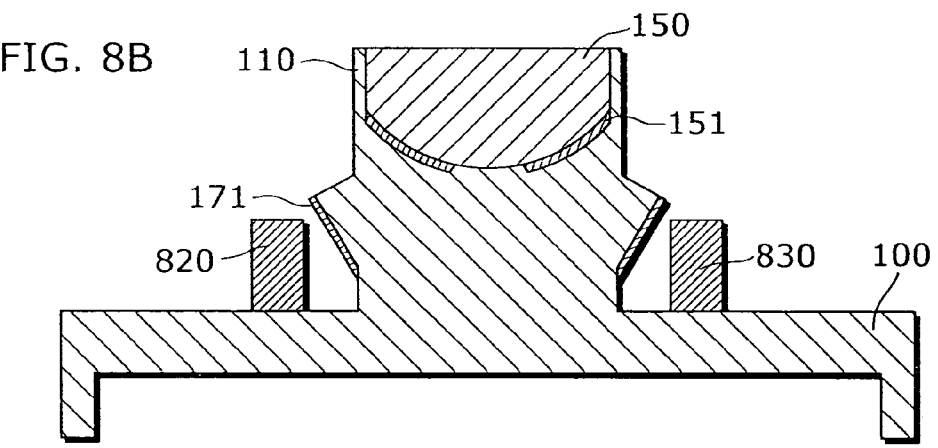
FIG. 8B is a cross sectional view of the second variation of the endoscope attachment according to the first embodiment.
Figure 8C:
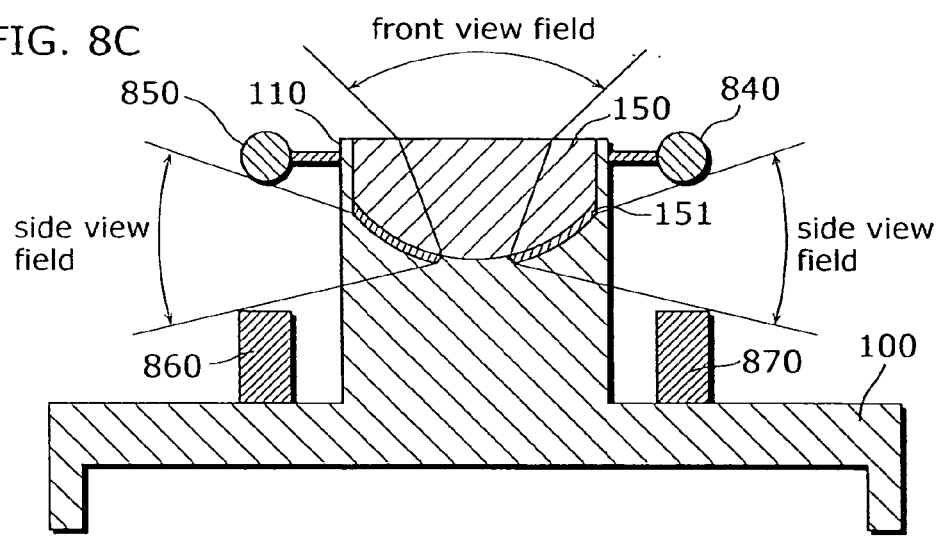
FIG. 8C is a cross sectional view of the third variation of the endoscope attachment according to the first embodiment.

Note that, as shown in FIG. 8B, rod lenses 820 and 830 may be formed on positions at a top surface of the attaching part 100, which corresponds to the positions of the lightings at the distal end of the endoscope. The rod lenses 820 and 830 are two frosted-glass cylinders for diffusing the illumination light from the prove to the areas at sides of the endoscope. In order to adjust directions of the light to be uniformly towards the area in front of the endoscope, a microlens array, a flat optical plate, or the like, for example, is equipped on the top surface of each of the rod lenses 820 and 830. Here, in order to efficiently diffuse the illumination light to the areas at the sides of the endoscope, a diffuse reflection surface or a mirror surface is formed on the sides of each of the rod lenses 820 and 830. Note that each of the rod lenses 820 and 830 may have a circular cone shape. Note also that, as shown in FIG. 8C, frosted-glass ball lenses 840 and 850 having respective diffusion surfaces may be arranged above the rod lenses 860 and 870 and outside the view angle of the front view field and the side view field. The rod lenses 860 and 870 leads the illumination light from the prove to the ball lenses 840 and 850, and the ball lenses 840 and 850 diffuse the led light to the areas at the sides of the endoscope. When the ball lenses 840 and 850 are arranged within the view angle of the front view field or the side view filed, a light shielding film, for example a black-painted film, is formed on parts of the surfaces of the ball lenses 840 and 850 facing the image capturing part 110, SO that the illumination light is prevented from being irradiated on the camera.

Figure 9:
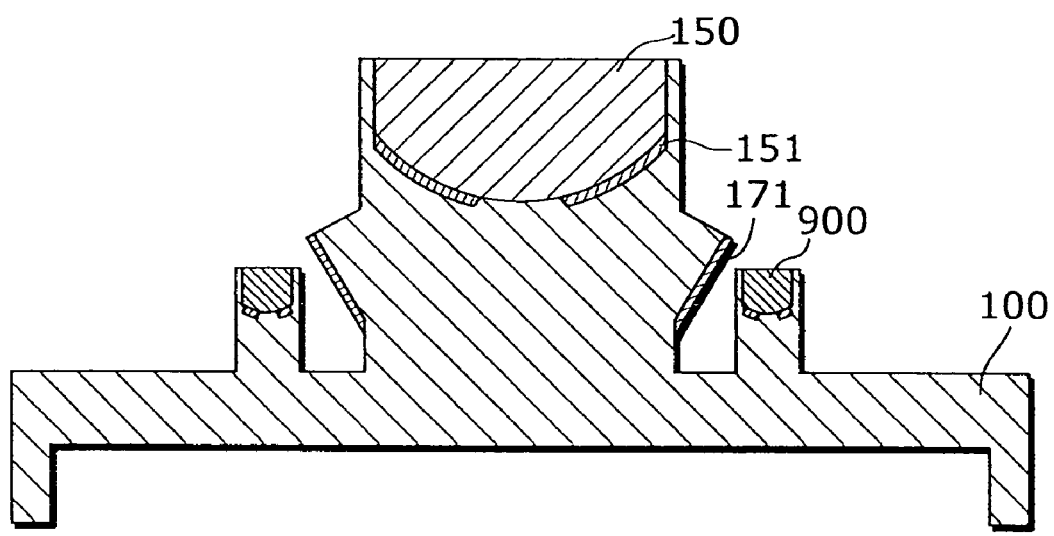
FIG. 9 is a cross sectional view of the fourth variation of the endoscope attachment according to the first embodiment.

Note also that, as shown in FIG. 9, a transparent member 900 may be formed at the top surface of the attaching part 100. The position of transparent member 900 corresponds to the position of the lighting at the distal end of the endoscope. The transparent member 900 has a hyperboloidal mirror for diffusing the illumination light from the probe to the areas at sides of the endoscope. Here, the hyperboloidal mirror has an opening from which the illumination light is provided to the area in front of the endoscope.

Note also that the wide angle lens 150 may have a spherical surface, not the hyperboloid, and a reflection film may be formed on the spherical surface.

Figure 10A:
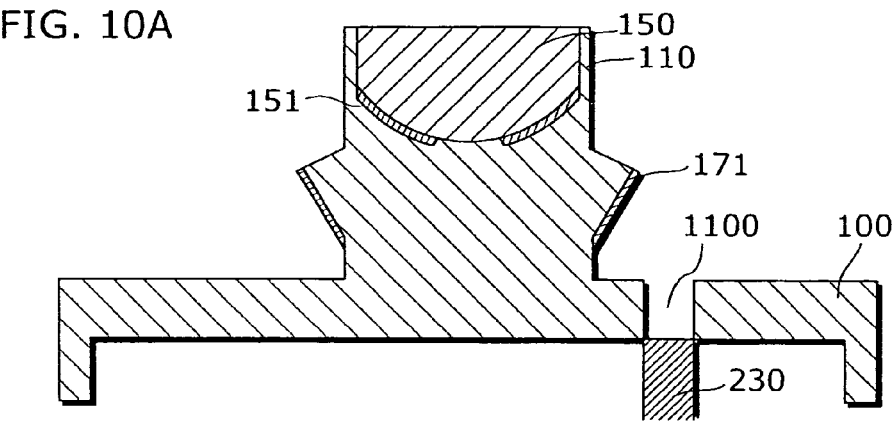
FIG. 10A is a cross sectional view of the fifth variation of the endoscope attachment according to the first embodiment.

Note also that, as shown in FIG. 10A, the attaching part 100 may have a hole 1100, so that any shielding does not exist in the front of the lighting 230 after the endoscope attachment being attached to the endoscope.

Figure 10B:
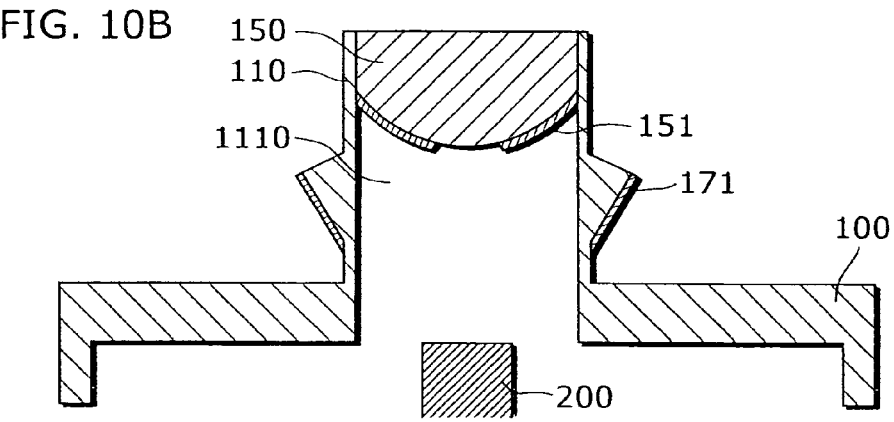
FIG. 10B is a cross sectional view of the sixth variation of the endoscope attachment according to the first embodiment.

Note also that, as shown in FIG. 10B, the image capturing part 110 may have a hollow 1110 which is positioned in front of the camera 200 after the endoscope attachment being attached to the endoscope.

Figure 10C:
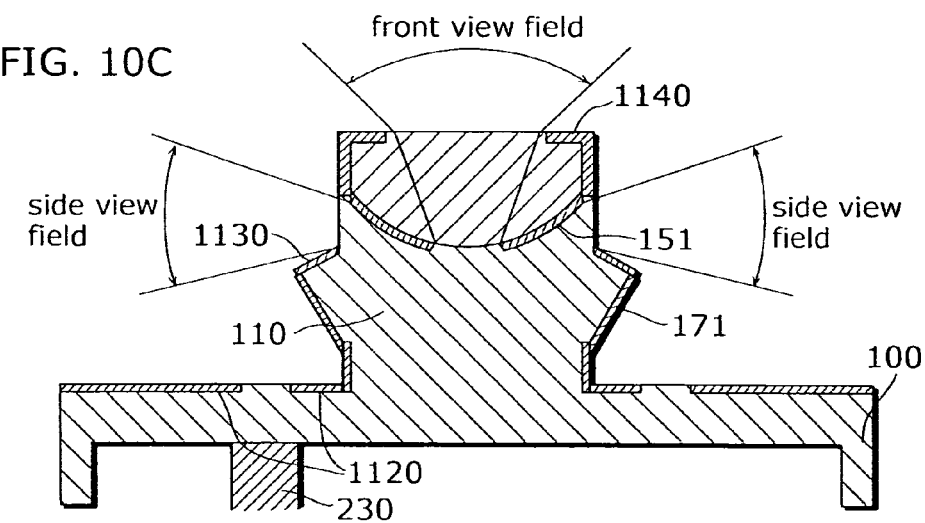
FIG. 10C is a cross sectional view of the seventh variation of the endoscope attachment according to the first embodiment.

Note also that light shielding films may be formed on surfaces except: the surface through which the lighting of the probe is taken in and out; the surface on which the incident light from the side view field is irradiated; the surface on which the incident light from the front view field is irradiated; the surface where the second mirror is formed. More specifically, as shown in FIG. 10C, the light shielding film 1120 may be formed on the top surface of the attaching part 100 except the surfaces through which the lighting 230 of the probe is taken in and out. Further, the light shielding film 1130 may be formed on the side surface of the image capturing part 110 except the surface on which incident light from the side view field is irradiated and the surface on which the second mirror 171 is formed. Furthermore, the light shielding film 1140 may be formed on the top surface of the image capturing part 110 except the surface on which the incident light from the front view field is irradiated.

Second Embodiment

Figure 11A:
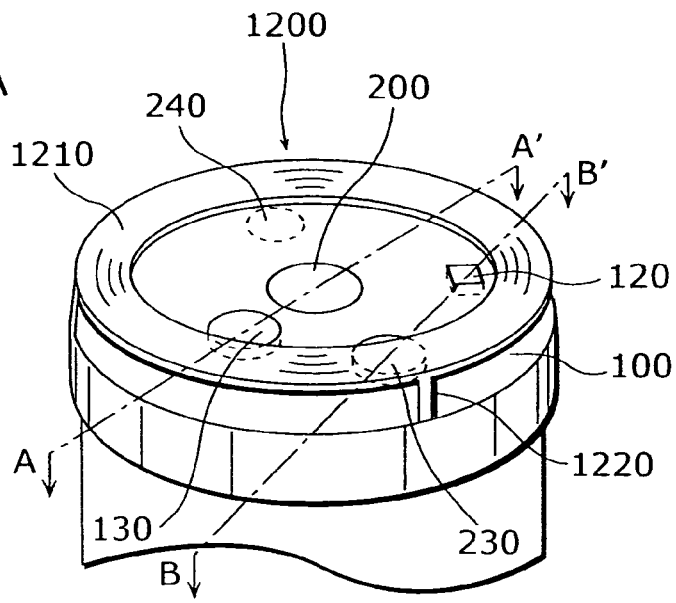
FIG. 11A is an external view of a distal end of a probe of an endoscope to which the endoscope attachment according to the second embodiment is attached.
Figure 11B:
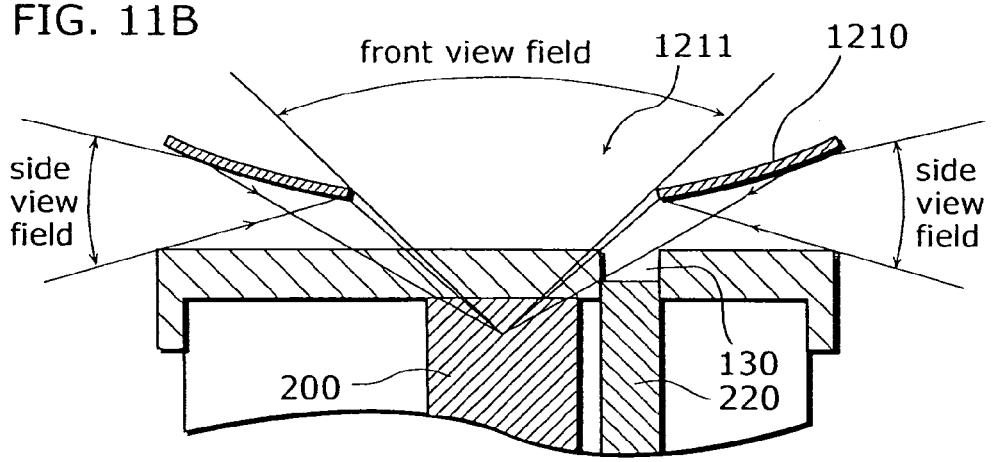
FIG. 11B is a cross sectional view (taken along line A-A' of FIG. 11A) of the distal end of the probe of the endoscope to which the endoscope attachment according to the second embodiment is attached.
Figure 11C:
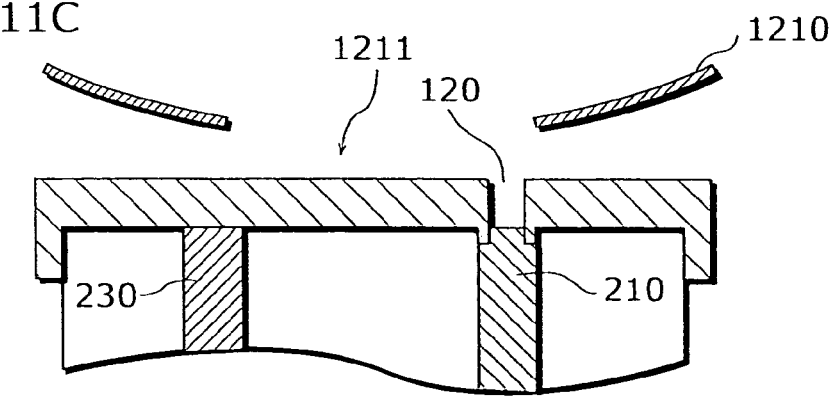
FIG. 11C is a cross sectional view (taken along line B-B' of FIG. 11A) of the distal end of the probe of the endoscope to which the endoscope attachment according to the second embodiment is attached.

FIG. 11A is an external view of a distal end of a probe of an endoscope to which an endoscope attachment according to the second embodiment is attached. FIGS. 11B and 11C are cross sectional views (taken along lines A-A' and B-B' of FIG. 11A) of the distal end of the probe of the endoscope to which the endoscope attachment is attached.

The endoscope attachment according to the second embodiment has: the flat-plate-shaped attaching part 100; and an image capturing part 1200 which is used to enable the camera of the probe to capture images, and formed on a surface of the attaching part 100 which is the opposite side of the surface contact with the distal end of the probe, in other words, on a top surface of the attaching part 100.

The image capturing part 1200 has: three (for example) support bars 1220 arranged along the outer periphery of the attaching part 100; and a convex mirror 1210 which has a ring shape and is fixed to the attaching part 100 by the support bars 1220. Note that the ring-shaped convex mirror 1210 fixed to the attaching part 100 may be a plane-shaped mirror.

Here, the mirror 1210 has a hyperboloid for reflecting the incident light from the wide-angle side view field to be irradiated on the camera. Thereby, a hyperboloidal mirror, which forms one sheet of the two-sheeted hyperboloid, is formed, so that, as shown in FIG. 11B, the wide-angle side view field is imaged on the image plane of the camera. Here, in order to enable the camera to capture image of an area in front of the endoscope, an opening 1211 is formed at center of the hyperboloid of the mirror 1210.

Furthermore, the mirror 1210 diffuses the illumination light from the probe to be provided to the areas at sides of the endoscope. Here, if all of the illumination light is irradiated on the mirror 1210, the illumination light is not provided to the area in front of the endoscope attachment, which makes it difficult to operate the probe. Therefore, a position and a size of the opening 1211 is adjusted, so that a part of the illumination light can be provided to the area in front of the endoscope attachment. Furthermore, in order to prevent regular reflection light of the illumination light from being irradiated on the mirror 1210, the opening 1211 is positioned at a part of the mirror 1210 where the illumination light is reflected regularly towards the camera. Further, in order not to disturb cleansing of the water injection nozzle 210 and taking in and out of the forceps, the opening 1211 is positioned at a part of the mirror 1210 which is in front of the water injection nozzle 210 and the forceps opening 220 and is in a range where the water injection nozzle 210 and the forceps can move. Note that the greater an outside diameter of the mirror 1210 is, the wider the side view field becomes, so that the outside diameter of the mirror 1210 is determined depending on a width of the necessary side view field. Note also that a curvature of the outer periphery of the mirror 1210 is determined depending on a maximum height of the mirror 1210 and a minimum elevation angle of the mirror 1210. Note also that a curvature of the opening 1211 of the mirror 1210 is determined so that the probe is not projected on the image plane. Note also that a diameter of the opening 1211 of the mirror 1210 is determined so that regular reflection light on the mirror surface is not irradiated on the image plane, and that a range where the forceps opening 220 can move is not restricted.

As described above, according to the endoscope attachment of the second embodiment, the mirror 1210 forms a hyperboloidal mirror. Thereby, a view angle of the side view field is enlarged to obtain images of an omnidirectional view field, thereby capturing images of not only the areas merely positioned at the sides of the endoscope, but also front and rear sides of folds. Thus, it is possible to realize an endoscope attachment which enables an endoscope to eliminate any blind areas and prevent a physician from overlooking nidus.

Further, according to the endoscope attachment of the second embodiment, the endoscope attachment has: the mirror 1210 which provides a part of the illumination light of the probe to the areas at sides of the endoscope attachment, and enables the camera 200 to capture images of the areas. Here, the mirror 1210 has the opening 1211 through which the camera 200 can capture the images of the area in front of the endoscope attachment. Thereby, the endoscope has the front view field and the side view field, and the illumination light can be provided in front and at the sides of the endoscope, so that it is possible to realize an endoscope attachment which enables the endoscope to have not only the imaging system but also a lighting suitable for the imaging system thereby capturing images of the areas in front of and at the sides of the endoscope.

Furthermore, according to the endoscope attachment of the second embodiment, the endoscope attachment is attached to the distal end of the probe of the endoscope and then used. Thereby, it is possible to realize an endoscope attachment which enables the endoscope to expand its functions easily and with a low cost.

Still further, according to the endoscope attachment of the second embodiment, the endoscope attachment has: the attaching part 100; and the image capturing part 1200. Thereby, the endoscope attachment has a simple structure, so that it is possible to realize an endoscope attachment which is easily cleansed thereby preventing spread of the disease to somebody else.

Still further, according to the endoscope attachment of the second embodiment, the opening 1211 is formed within an area of the mirror 1210 where the illumination light from the mirror 1210 is reflected regularly to the camera. Thereby, the illumination light emitted from the probe is prevented from being irradiated on the camera as incident light, so that it is possible to realize an endoscope attachment which prevents a part of image captured by the endoscope from being too brightened.

Still further, according to the endoscope attachment of the second embodiment, the endoscope attachment has the holes 120 and 130, and the position of the camera 200 is adjusted to be fit to the image capturing part 110, by engaging the water injection nozzle 210 and the forceps opening 220 of the endoscope with the holes 120 and 130. Thereby, complicated processes are not necessary to attach the endoscope attachment to the endoscope, so that it is possible to realize an endoscope attachment which is easily attached to the endoscope.

Third Embodiment

Figure 12A:
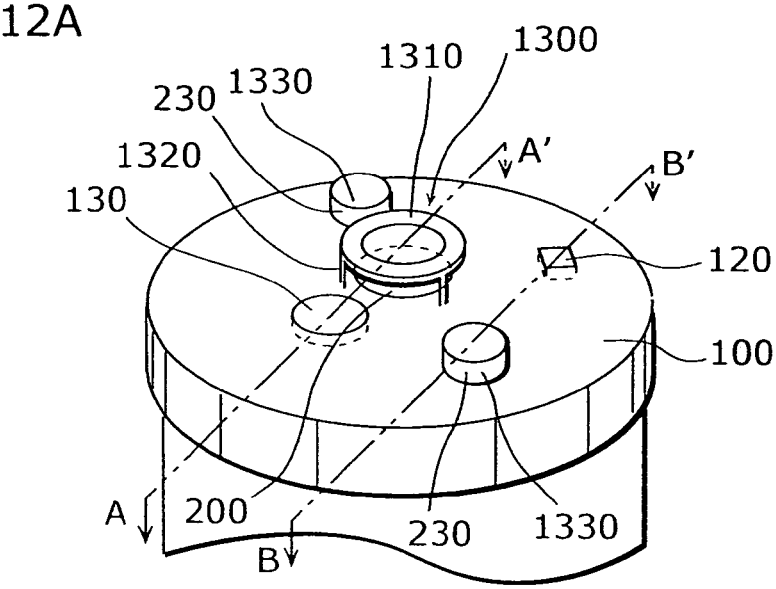
FIG. 12A is an external view of a distal end of a probe of an endoscope to which the endoscope attachment according to the third embodiment is attached.
Figure 12B:
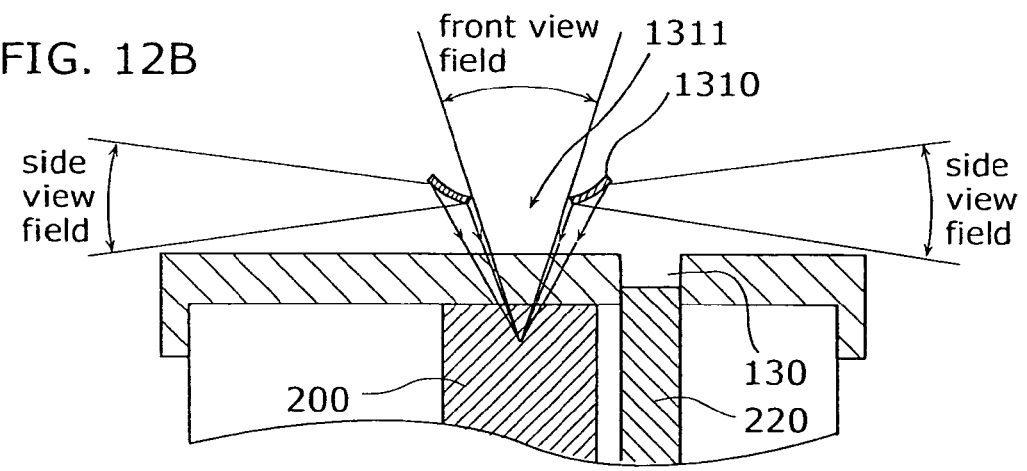
FIG. 12B is a cross sectional view (taken along line A-A' of FIG. 12A) of the distal end of the probe of the endoscope to which the endoscope attachment according to the third embodiment is attached.
Figure 12C:
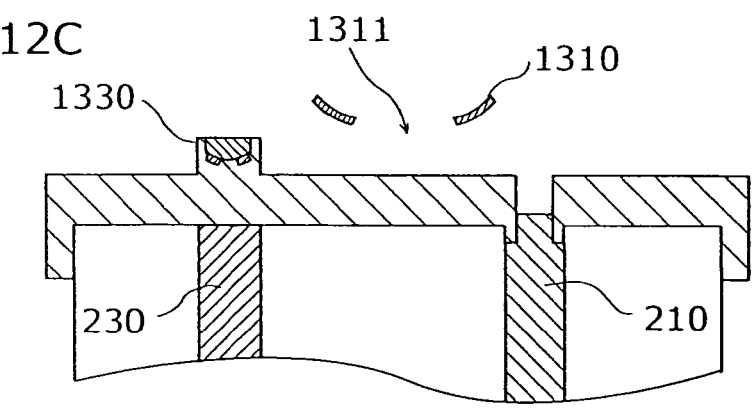
FIG. 12C is a cross sectional view (taken along line B-B' of FIG. 12A) of the distal end of the probe of the endoscope to which the endoscope attachment according to the third embodiment is attached.

FIG. 12A is an external view of a distal end of a probe of an endoscope to which the endoscope attachment according to the third embodiment is attached. FIGS. 12B and 12C are cross sectional views (taken along lines A-A' and B-B' of FIG. 12A) of the distal end of the probe of the endoscope to which the endoscope attachment.

The endoscope attachment according to the third embodiment has: the flat-plate-shaped attaching part 100; an image capturing part 1300 which is used to enable the camera of the probe to capture images, and formed on a surface of the attaching part 100 which is the opposite side of the surface contact with the distal end of the probe, in other words, on a top surface of the attaching part 100; and a transparent member 1330 formed on the top surface of the attaching part 100 at a position corresponding to the position of the lighting at the distal end of the endoscope.

The image capturing part 1300 has: multiple (three, for example) support bars 1320; and a convex mirror 1310 which has a ring shape and is fixed to the attaching part 100 by the support bars 1320. The image capturing part 1300 is arranged to be positioned above the camera 200 only.

Here, the mirror 1310 has a hyperboloid for reflecting the incident light from the wide-angle side view field to be irradiated on the camera. Thereby, a hyperboloidal mirror, which forms one sheet of the two-sheeted hyperboloid, is formed, so that, as shown in FIG. 12B, the wide-angle side view field is imaged on the image plane of the camera. Here, in order to enable the camera to capture image of an area in front of the endoscope, an opening 1311 is formed at center of the hyperboloid of the mirror 1310.

The transparent member 1330 has a hyperboloidal mirror for diffusing the illumination light from the probe to the areas at the sides of the endoscope. Here, the hyperboloidal mirror has an opening 1311 for providing the illumination light to the area in front of the endoscope.

As described above, according to the endoscope attachment of the third embodiment, the mirror 1310 forms a hyperboloidal mirror. Thereby, a view angle of the side view field is enlarged to obtain capture images of an omnidirectional view field, thereby capturing images of not only the areas merely positioned at the sides of the endoscope, but also front and rear sides of folds. Thus, it is possible to realize an endoscope attachment which enables the endoscope to eliminate any blind areas and prevent a physician from overlooking nidus.

Further, according to the endoscope attachment of the third embodiment, the endoscope attachment has: the transparent member 1330 which provides a part of the illumination light of the probe to the areas at sides of the endoscope attachment; and the mirror 1310 which enables the camera 200 to capture images of the areas. Here, the mirror 1310 has the opening 1311 through which the camera 200 can capture the images of the area in front of the endoscope attachment. Thereby, the endoscope has the front view field and the side view field, and the illumination light can be provided in front and at the sides of the endoscope, so that it is possible to realize an endoscope attachment which enables the endoscope to have not only the imaging system but also a lighting suitable for the imaging system thereby capturing images of the areas in front of and at the sides of the endoscope.

Furthermore, according to the endoscope attachment of the third embodiment, the endoscope attachment is attached to the distal end of the probe of the endoscope and then used. Thereby, it is possible to realize an endoscope attachment which enables the endoscope to expand its functions easily and with a low cost.

Still further, according to the endoscope attachment of the third embodiment, the endoscope attachment has: the attaching part 100; the image capturing part 1300; and the transparent member 1330. Thereby, the endoscope attachment has a simple structure, so that it is possible to realize an endoscope attachment which is easily cleansed thereby preventing spread of the disease to somebody else.

Still further, according to the endoscope attachment of the third embodiment, the endoscope attachment has the holes 120 and 130, and the position of the camera 200 is adjusted to be fit to the image capturing part 110, by engaging the water injection nozzle 210 and the forceps opening 220 of the endoscope with the holes 120 and 130. Thereby, complicated processes are not necessary to attach the endoscope attachment to the endoscope, so that it is possible to realize an endoscope attachment which is easily attached to the endoscope.

While the endoscope attachment according to the present invention has been described having reference to the above preferred embodiments, those having skill in the art will appreciate that the present invention is not limited to the above embodiments and other variations and modifications may be made without departing from the spirit and scope of the present invention.

Figure 13A:
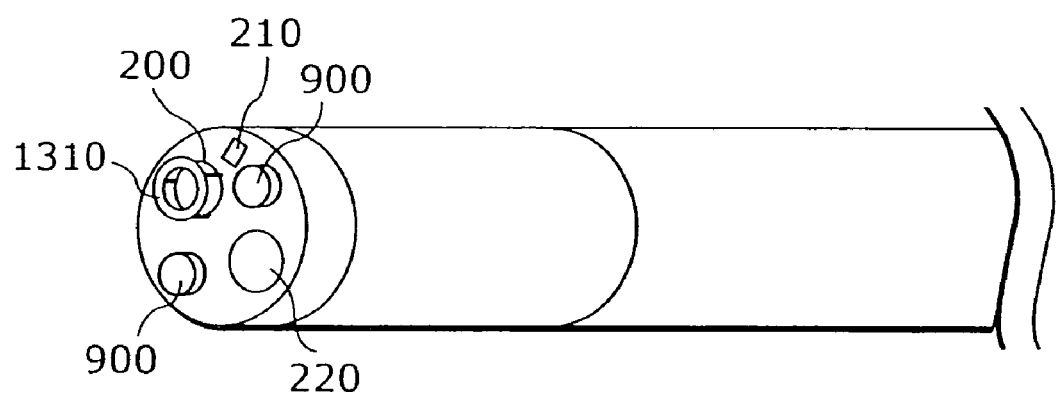
FIG. 13A is an external view of a probe of the endoscope according to the present invention.
Figure 13B:
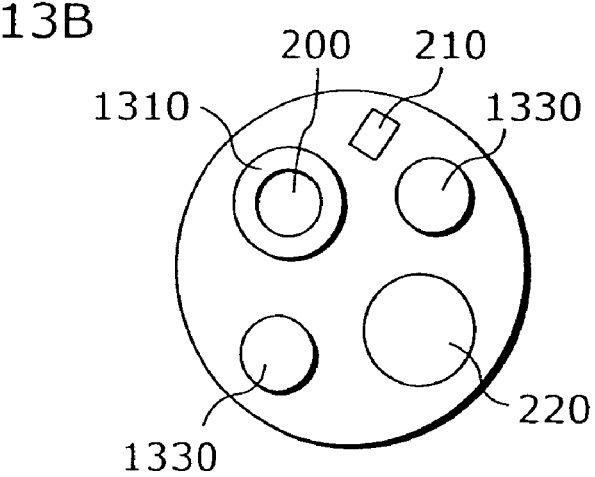
FIG. 13B is a top view of a distal end of a probe of the endoscope according to the present invention.
Figure 14A:
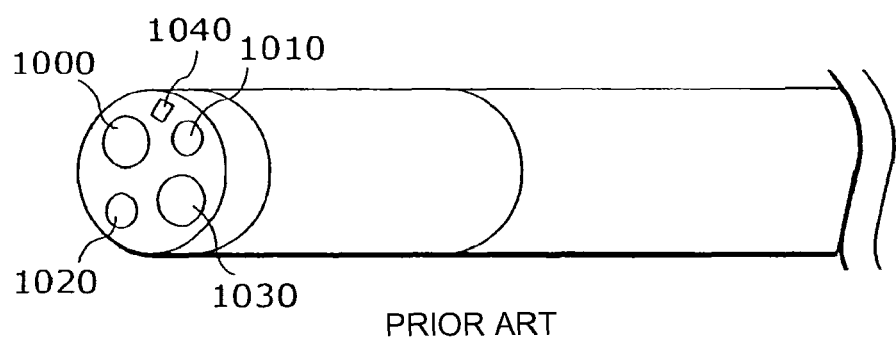
FIG. 14A is an external view of a probe of the conventional endoscope.
Figure 14B:
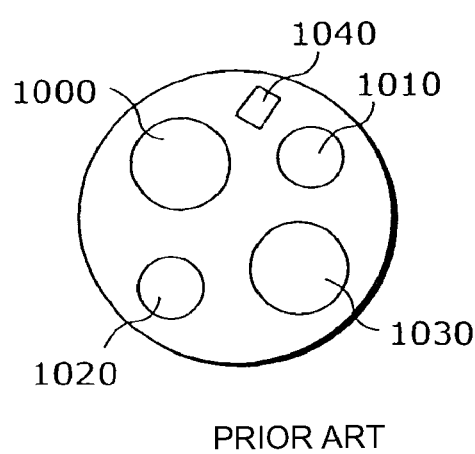
FIG. 14B is a top view of a distal end of a probe of the endoscope of the conventional endoscope.

For example, the present invention may be an endoscope whose probe has a distal end having a structure of the endoscope attachment according to the present invention. More specifically, the present invention may be an endoscope whose probe has a distal end having: the convex mirror 1310 which has a ring shape and is fixed to the distal end of the endoscope by the three support bars 1320, so that the convex mirror 1310 is positioned above the camera 200 only; and the transparent members 1330 each of which is formed at a position corresponding to the position of each lighting, as shown in an external view of FIG. 13A and a top view of FIG. 13B.

The present invention is able to be used as an endoscope attachment, and especially as an endoscope attachment or the like which is attachable to an endoscope for imaging the inside of digestive organs.

The invention claimed is:

1. An endoscope attachment which is attachable to a distal end of a probe of an endoscope used to image a digestive organ, the endoscope attachment comprising:
   a view field obtaining part operable to obtain a front view field and a side view field for the probe; and
   a convex-shaped illumination light providing part operable to diffuse illumination light illuminating an area in front of the probe in order to provide the illumination light to an area at a side of the endoscope attachment,
   wherein the view field obtaining part is a mirror having an opening,
   an image of an area at a side of the probe is captured by a camera of the probe via the mirror,
   an image of an area in front of the probe is captured by the camera through the opening of the mirror, and
   the convex-shaped illumination light providing part is a ring-shaped mirror which is used as the view field obtaining part.

2. The endoscope attachment according to claim 1, wherein the mirror also has a convex shape.

3. The endoscope attachment according to claim 1, wherein the opening of the mirror is positioned at a range where forceps are moveable.

4. The endoscope attachment according to claim 1, wherein the endoscope attachment has a support member that secures the mirror to the endoscope attachment.

5. The endoscope attachment according to claim 1, wherein the opening is positioned at an area of the mirror, and the illumination light is regularly reflected on the area to the camera.

6. The endoscope attachment according to claim 1, further comprising,
   a transparent attaching part having two through-holes and operable to attach the endoscope attachment to the probe,
   wherein relative positions of the two through-holes in the transparent attaching part correspond to relative positions of a forceps opening and a water injection nozzle of the probe, respectively.

7. The endoscope attachment according to claim 1 wherein the view field obtaining part is operable to obtain an omnidirectional view field for the probe.

8. An endoscope which is used to image a digestive organ, the endoscope comprising:
   a view field obtaining part, which is arranged at a distal end of a probe of the endoscope, operable to obtain a front view field and a side view field for the probe; and
   a convex-shaped illumination light providing part, which is arranged at the distal end of the probe of the endoscope, operable to diffuse illumination light illuminating an area in front of the probe in order to provide the illumination light to an area at a side of the endoscope,
   wherein the view field obtaining part is a mirror having an opening,
   an image of an area at a side of the probe is captured by a camera of the probe via the mirror,
   an image of an area in front of the probe is captured by the camera through the opening of the mirror, and
   the convex-shaped illumination light providing part is a ring-shaped mirror which is also used as the view field obtaining part.

* * * * *